US010780246B2

(12) United States Patent
Yao et al.

(10) Patent No.: US 10,780,246 B2
(45) Date of Patent: Sep. 22, 2020

(54) VASCULAR MICROCATHETER

(71) Applicant: CALLISYN BIOMEDICAL, INC., North Andover, MA (US)

(72) Inventors: Fei Yao, North Andover, MA (US); Xiaowei Sun, North Andover, MA (US)

(*) Notice: Subject to any disclaimer, the term of this patent is extended or adjusted under 35 U.S.C. 154(b) by 0 days.

(21) Appl. No.: 14/484,883

(22) Filed: Sep. 12, 2014

(65) Prior Publication Data
US 2016/0074621 A1    Mar. 17, 2016

(51) Int. Cl.
*A61M 25/00* (2006.01)
*A61M 25/01* (2006.01)

(52) U.S. Cl.
CPC .... *A61M 25/0053* (2013.01); *A61M 25/0021* (2013.01); *A61M 25/0045* (2013.01); *A61M 25/0108* (2013.01); *A61M 2025/0042* (2013.01); *A61M 2025/0047* (2013.01); *A61M 2025/0059* (2013.01)

(58) Field of Classification Search
CPC ............ A61K 31/717; A61M 25/0012; A61M 25/0045; A61M 25/0053; A61M 25/0054; A61M 25/0097; A61M 25/0138; C08J 2301/12
See application file for complete search history.

(56) References Cited

U.S. PATENT DOCUMENTS

| | | |
|---|---|---|
| 3,959,429 A | 5/1976 | Benning |
| 4,459,255 A | 7/1984 | Sheridan |
| 4,929,242 A * | 5/1990 | Desecki .......... A61M 25/0017 604/266 |
| 5,037,404 A | 8/1991 | Gold et al. |
| 5,041,100 A | 8/1991 | Rowland et al. |

(Continued)

FOREIGN PATENT DOCUMENTS

| | | |
|---|---|---|
| CN | 101810587 | 8/2010 |
| EP | 1062965 | 12/2000 |

(Continued)

OTHER PUBLICATIONS

K. V. Sharma, M. R. Dreher, Y. Tang, W. Pritchard, O. A. Chiesa, J. Karanian, J. Peregoy, B. Orandi, D. Woods, D. Donahue, J. Esparza, G. Jones, S. L. Willis, A. L. Lewis and B. J. Wood, "Development of Image-able Beads for Transcatheter Embolotherapy," J Vasc Interv Radiol., vol. 21, No. 6, pp. 865-876, Jun. 2010.*

(Continued)

*Primary Examiner* — Laura A Bouchelle
*Assistant Examiner* — Justin L Zamory
(74) *Attorney, Agent, or Firm* — Grossman, Tucker, Perreault & Pfleger, PLLC

(57) ABSTRACT

There is provided a microcatheter with a tapering wall thickness shaft having varying stiffness/flexibility along its length from proximal end near the medical practitioner to the distal end near the target site in the patient, such as with at least three segments. The shaft is prepared of a thermoplastic material having varying composition along its length. The distal end may be shaped according to the required use just prior to the medical procedure. The microcatheter is particularly adapted for the delivery of microspheric compositions for treatment of tumors or fibroids by embolization of peripheral blood vessels of the tumor or fibroid.

11 Claims, 10 Drawing Sheets

(56) References Cited

U.S. PATENT DOCUMENTS

| | | |
|---|---|---|
| 5,163,431 A | 11/1992 | Griep |
| 5,254,107 A | 10/1993 | Soltesz |
| 5,489,270 A | 2/1996 | Van Erp |
| 5,514,236 A | 5/1996 | Avellanet et al. |
| 5,591,142 A | 1/1997 | Van Erp |
| 5,624,396 A | 4/1997 | McNamara et al. |
| 5,658,263 A | 8/1997 | Dang et al. |
| 5,736,085 A | 4/1998 | Brown et al. |
| 5,789,018 A | 8/1998 | Engelson et al. |
| 5,843,050 A | 12/1998 | Jones et al. |
| 5,843,356 A | 12/1998 | Patel et al. |
| 5,906,618 A | 5/1999 | Larson, III |
| 5,976,120 A | 11/1999 | Chow et al. |
| 5,997,487 A | 12/1999 | Kolehmainen et al. |
| 6,078,830 A | 6/2000 | Levin et al. |
| 6,217,565 B1 | 4/2001 | Cohen |
| 6,254,588 B1 | 7/2001 | Jones et al. |
| 6,248,082 B1 | 9/2001 | Jafari |
| 6,306,124 B1 | 10/2001 | Jones et al. |
| 6,355,027 B1 | 3/2002 | Le et al. |
| 6,503,244 B2 | 1/2003 | Haymann |
| 6,533,751 B2 | 3/2003 | Cragg et al. |
| 6,547,768 B2 | 4/2003 | Trotta |
| 6,689,120 B1 | 2/2004 | Gerdts |
| 6,699,222 B1 | 3/2004 | Jones et al. |
| 6,964,657 B2 | 11/2005 | Cragg et al. |
| 8,382,738 B2 | 2/2013 | Simpson et al. |
| 8,658,214 B2 | 2/2014 | Rodriquez et al. |
| 2002/0138093 A1 | 9/2002 | Song et al. |
| 2004/0153049 A1* | 8/2004 | Hewitt ............... A61M 25/0012 604/527 |
| 2005/0175665 A1* | 8/2005 | Hunter .................. A61K 45/06 424/423 |
| 2005/0175709 A1* | 8/2005 | Baty, III .......... A61B 17/12022 424/489 |
| 2007/0237956 A1 | 10/2007 | Figuly et al. |
| 2009/0149831 A1* | 6/2009 | Kaul ..................... A61F 5/0089 604/511 |
| 2010/0049165 A1 | 2/2010 | Sutherland et al. |
| 2010/0130925 A1 | 5/2010 | Haslinger et al. |
| 2012/0183949 A1* | 7/2012 | Hyde ..................... A61B 5/082 435/5 |
| 2013/0190795 A1* | 7/2013 | Matson ............... A61L 24/0036 606/191 |

FOREIGN PATENT DOCUMENTS

| | | |
|---|---|---|
| EP | 2450077 | 5/2012 |
| JP | 2011-125737 | 6/2011 |
| WO | 96/15819 | 5/1996 |

OTHER PUBLICATIONS

Bullman et al., "Current Concepts in Uterine Fibroid Embolization", Radiographics, 2012, vol. 32, pp. 1735-1750. Washington, D.C.

Pron et al., "Technical Results and Effects of Operator Experience on Uterine Artery Embolization for Fibroids: The Ontario Uterine Fibroid Embolization Trial", Journal of Vascular and Interventional Radiology, 2003, vol. 14, pp. 545-554. Ontario, Canada.

International Search Report and Written Opinion from related PCT Application No. PCT/US15/49577, dated Dec. 14, 2015.

Extended Search Report from related EPO Appln. No. 15839935.2, dated Apr. 30, 3018.

* cited by examiner

VASCULAR MICROCATHETER

TECHNICAL FIELD

The present invention relates to vascular microcatheter and more particularly, to a microcatheter to reach peripheral blood vessels for drug delivery and embolic treatment.

BACKGROUND INFORMATION

There is a variety of clinical conditions in which occluding blood vessels may be desirable, such as for the treatment of aneurysm, treatment of tumor, or bleeding. In cancer treatment, where the tumor is hard to reach and cannot be resected, occluding blood flow to the tumor may be a preferred alternative. However, navigating the vascular system to reach the site of the tumor may be difficult. Many catheters have been developed to overcome these difficulties, such as catheters having differing flexibility between the proximal and distal ends of the catheter shaft, catheter having narrowing diameter over the length of the catheter, catheter with flexible tips, catheter with coatings for easing the ingress of the shaft in the vascular blood vessels, or the introduction and withdrawal of the guide wire in the lumen of the shaft, or delivery of compositions or materials through the lumen of the shaft to a site in a patient, etc. When drugs, composition or materials need to be deposited at the site in need of treatment, current catheters may clog easily or require high shear to deliver the drug, composition or material at the desired site in the patient.

Accordingly, there is still a need for new designs of flexible catheters that can deliver with ease drugs, compositions or solid materials to a specific site in a patient such as a human and in a precise and efficient manner.

SUMMARY

Therefore, there is provided a medical instrument for accessing a blood vessel of a patient such as a microcatheter with a shaft having varying stiffness/flexibility along its length from proximal end near the medical practitioner to the distal end near the target site in the patient, such as from relatively stiff to relatively flexible over at least three regions.

In an embodiment of the invention, a medical instrument for accessing a blood vessel of a patient may include a hub having a proximal and distal end, a luer adapter disposed at the proximal end for connecting with medical equipment, and a shaft extending from the hub distal end, the shaft having a lumen and having a tapering wall, at least three braid sections having different winding pitches. The catheter also may include a hydrophilic exterior coating and a lubricious internal liner. The tapering wall itself has a varying flexibility along its length from relatively stiffer at the proximal end as reflected by a relatively high Shore D value (60D-75D) and a relatively lower flexibility at the distal end having as reflected by a relatively lower Shore D value (30D to 40D).

Accordingly, the wall of the shaft itself may have varying flexibility along its length from relatively stiffer at the proximal end to relatively more flexible at the distal end, as reflected by different Shore D Hardness values. Such values may vary from 75D to 30D over the length of the shaft from the proximal end to the distal end. Thus the microcatheter is relatively easy to manipulate. This can be measured by using the Trackability Evaluation System including Temperature Controller, Gripping Fixture, Trackability Evaluation Fixture Control Panel, Manual Gripper, Force Gage; and Arteries and Vessels Models.

The shaft of the catheter has a first braid section with a winding pitch of 100-130 PPI, a second braid section with a winding pitch of 130-150 PPI, and a third braid section with a winding pitch of 160-180 PPI. The winding pitch includes all individual values within such ranges, which vary by 1.0 PPI. For example, a first braid section has a winding pitch of 115-125 PPI, a second braid section has a winding pitch of 140-150 PPI, and a third braid section has a winding pitch of 160-170 PPI. Braid wire density is described as picks per inch (PPI), which is the number of wire crossovers per inch of shaft.

In yet other embodiments, the shaft further includes at least three segments having differing material composition. Certain compositions for the shaft along the length vary from relatively flexible at the distal end to relatively stiff at the proximal end. In some embodiments, the lumen has a lubricious lining material. In one embodiment, the lining material is polytetrafluoroethylene (PTFE). In another embodiment, the shaft has an outer diameter at its distal end of 0.0425.

In other embodiments, there is provided methods of accessing blood vessels in a patient including inserting a catheter according to the invention as described above in all its variants, into the femoral artery of a patient, navigating or directing the distal end of the catheter to a site of treatment in the blood vessel of a patient and injecting a composition comprising microspheres having an average size of 75-500 μm at the treatment site.

In some embodiments, the microspheres comprise a crosslinked copolymer of cellulose acetate and a hydrophilic polymer. In certain embodiments, the hydrophilic polymer may be selected from a poly alkylene glycol, polysaccharide, glucosaminoglycan, and modified cellulose. In other embodiments, the hydrophilic polymer may be selected from hydroxymethyl cellulose, chitosan, amylose, cellulose acetate, and polyvinyl alcohol. In yet other embodiments, the microsphere may further include a dye or a therapeutic agent.

In still other embodiments, the site of treatment may be an artery in the liver, heart, kidney, or uterus. In some embodiments, the site of treatment may be a blood vessel in a tumor or fibroid. In some other embodiments, the method of treatment may include injecting an anticoagulant. In yet other embodiments, the method of treatment may include microspheres include a fluoroscopic agent. In some other embodiments, the method of treatment may include imaging blood vessels at the site of treatment.

BRIEF DESCRIPTION OF THE DRAWINGS

These and other features and advantages will be better understood by reading the following detailed description, taken together with the drawings wherein.

DETAILED DESCRIPTION

Figure 1:
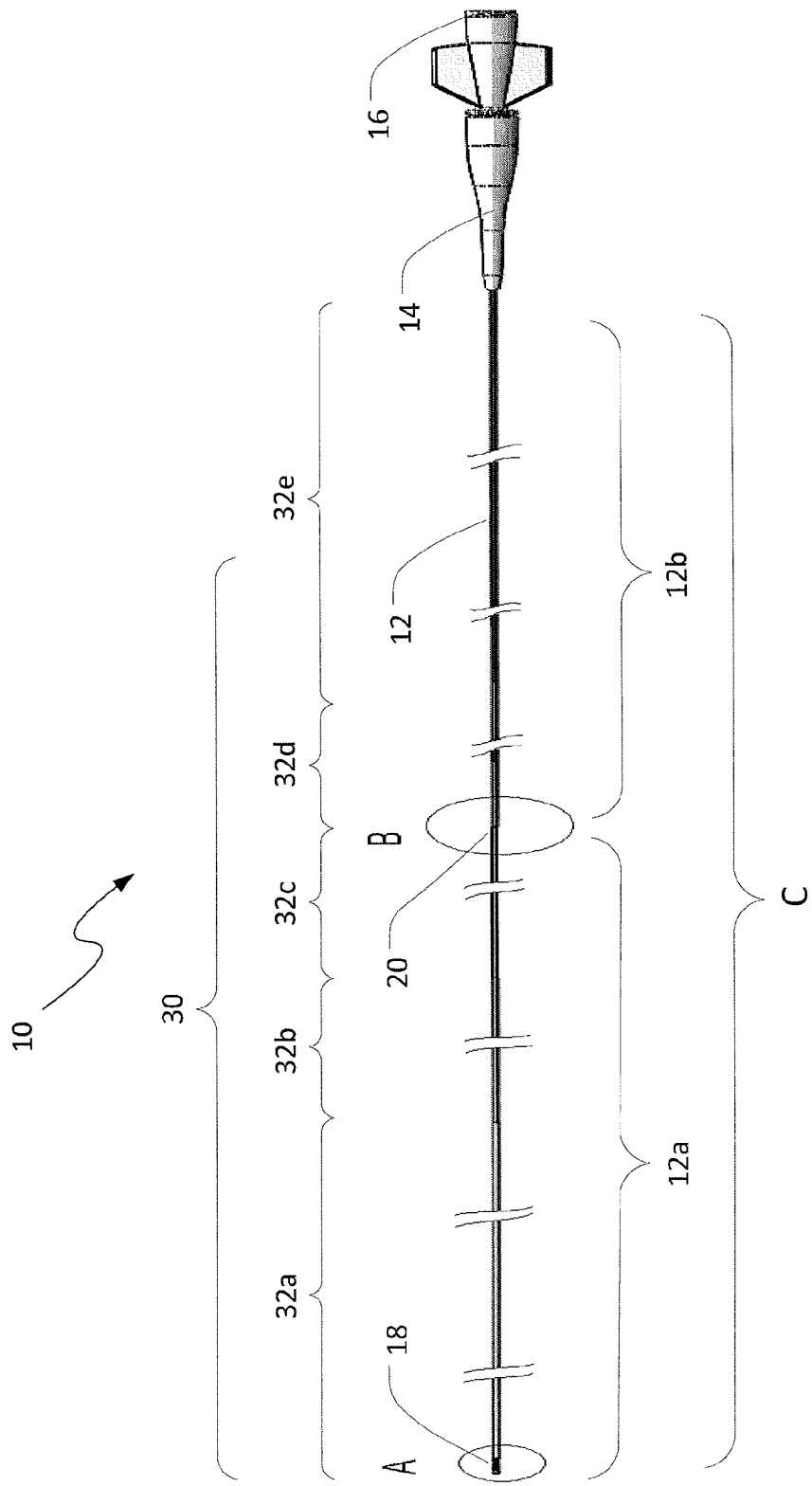
FIG. 1 is a side view of a schematic representation of a microcatheter according to an embodiment of the invention.

Referring to FIG. 1, a microcatheter 10 according to the invention may include a shaft 12 connected to a hub 14 at the proximal end. The hub 14 may be equipped with a female luer adapter 16 to connect the catheter 10 to other medical equipment, such as a syringe or tube to insert a guidewire or inject a fluid into the catheter 10. The shaft 12 extends from the hub 14 at the proximal end to the end piece 18 at the distal end. The shaft may be constructed in several segments, e.g. 12a and 12b, which may be connected at a junction 20, for ease of assembly (see also FIG. 1B) of several outer diameter size segments. The wall 32 of the catheter may be extruded from a variety of materials along its length, in multiple regions, such as from 3 to 7 regions, typically 5, see 32a, 32b, 32c, 32d, and 32e. The relative hardness and rigidity of the wall sections may then vary, from relatively higher hardness/rigidity for wall section 32e at the proximal end (Shore D of 60D-75D) and discretely lower wall hardness/rigidity values as one proceeds from section 32e, to section 32d, to section 32c, to section 32b and to section 32a at the distal end (Shore D of 30D to 40D). Accordingly, if one starts with a relatively high Shore D value for section 32e, one may successively and discretely lower the Shore D values as proceeding from section 32e, to section 32d, to section 32c, to section 32b and to section 32a. Each section may therefore have a drop in Shore D values, such as a drop of 1-5 on the Shore D scale. On the other hand, as discussed herein, the catheter shaft 12 includes braiding reinforcement which proceeds from relatively low pitch at the proximal end to relatively high pitch at the distal end.

The use of at least 3 distinct regions having differing flexibility facilitates the introduction and navigation of the catheter tip inside the contoured and branching blood vessels while providing stability at the proximal end, hence relatively better handling. For example, catheter wall 32 may preferably be made of thermoplastic extrudable polymer such as the material sold under the trademark PEBAX™, which is a nylon block copolymer, more specifically, a copolymer of nylon and polyethylene oxide, which is available from Arkema Specialty Polyamides, France. More specifically, it is preferred to utilize the materials sold under the trademark PEBAX30D, PEBAX45D, PEBAX55D and PEBAX72D, which amount to nylon block copolymers with, respectively, Shore D Hardness values of about 30D, 45D, 55D and 72D. Other suitable materials include for example nylon-12 type materials (Shore D 75), which are available from Foster Polymers, Connecticut, USA.

The wall may also contain fillers from about 5 to 25% by weight, typically 20% by weight, such as barium sulfate or titanium dioxide. The wall may also contain pigments or dyes to identify various configurations of the catheter. The length of each region 32a to 32e may be adjusted for optimum handling. For example the length of region 32a may be from 2.0 to 8.0 inches and any 0.1 increment in between, typically 6.7 inches; the length of regions 32b to 32d may independently be from 0.5 to 3.0 inches and any 0.1 increment in between, typically 1.6 inches. The length of region 32e may be from 30.0 to 50.0 inches and any 0.1 increment in between, typically 39.8 inches. The total length of the shaft (12a and 12b) may be from 35.0 in to 60.0 inches, any 0.1 increment in between, typically 43.3 inches (110 cm) or 51.2 inches (130 cm).

Figure 1A:
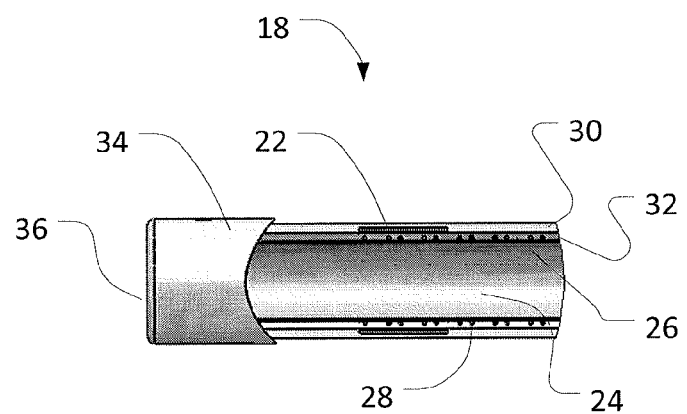
FIG. 1A is a side view of in partial cross section of a schematic representation of a distal end of a microcatheter shaft according to an embodiment of the invention.

Referring to FIG. 1A, the catheter shaft (12a and 12b) includes a lumen 24, which may include a liner 26 of lubricious material to facilitate the movement of a guidewire. The lubricious material may have a lubricity/friction force of 50 g or less, such as PTFE (polytetrafluoroethylene) . Such force was measured by Lubricity Friction Pinch Test under conditions as follows: (1) Test cycles: 15; (2) Maximum (Peak) force≤50 g for each of the cycles; (3) Clamp force: 500 g; and (4) Pull Speed: 1.0 cm/sec. Other suitable materials include for example polyethylene, polyester polyether block copolymer, chlorinated polyolefin, FEP, PFA, ETFE, SEBS, silicone and polyamide. The layer 26 may have a thickness of 0.0001 inches to 0.001 inches, typically 0.0005 inches.

The end piece of the catheter 18 may include a radiopaque band 22 to help position the end piece of the catheter 18 to the desired site in a patient body for the delivery of the treatment. The radiopaque band 22 may be made of platinum enriched with iridium, such as 2 to 20% by weight, typically 10% by weight. The end piece of the catheter 18 may be made of a relatively low temperature thermoplastic material to allow the practitioner to shape it with a mandrel to adapt for the specific procedure immediately prior to use. Typically, a medical practitioner would select a mandrel for a desired shape and apply heat of about 150° F. to 200° F. with steam. The end piece of the catheter 18 may further include a cap 34 made of copper and having a rounded edge 36. The wall 32 of the catheter shaft 12 may include braids 28 (see FIG. 1C below). The wall 32 of the catheter shaft 12 may be covered by a hydrophilic coating layer 30. The hydrophilic coating was done by Lubricent® UV Hydrophilic Coating from Harland Medical Systems. The coating thickness was measured by calculating the difference of un-hydrated and hydrated catheters. Typically the thickness of a hydrophilic coated catheter ranges from 0.1-80 µm, preferably 1-50 µm, more preferably 10-30 µm. This performance enhances the device's ability to navigate through tortuous anatomical pathways while reducing tissue damage and adding to patient comfort.

Figure 1B:
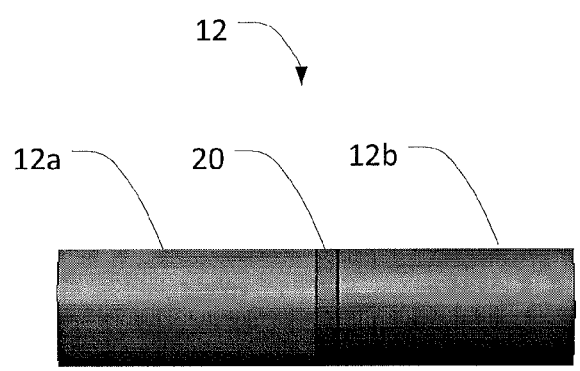
FIG. 1B is a side view of a schematic representation of an intermediate section of a microcatheter shaft according to an embodiment of the invention.

Referring to FIG. 1B, the catheter shaft 12 may be assembled in at least two sections 12a and 12b, connected at a junction 20. The thickness of the wall 32 may be varied also along the length of the shaft 12, or per sections, such as the sections 12a and 12b of the shaft 12. The thickness of the wall for each section (12a, 12b) may be selected from 0.005 inches to 0.0030 inches and any value therein, in 0.001 inch increments.

The outside diameter of the shaft 12 may be constant or increasing from distal end to proximal end, typically not more than 0.05 inches, from 0.020 inches to 0.0475 inches. For example, it may be 0.0425 inches for section 12a and 0.0445 inches for section 12b (i.e. 2.7 Fr at the distal end and 2.9 Fr at the proximal end).

The lumen 24 may be uniform along the length of the shaft 12 and large enough to accommodate a guide wire of 0.021 inches in diameter, typically the lumen may be 0.025 to 0.35 inches internal diameter, preferably 0.25 inches being sufficient. The usable length of the shaft 12 may be selected from 100 cm to 150 cm, typically 110 cm or 130 cm.

Figure 1C:
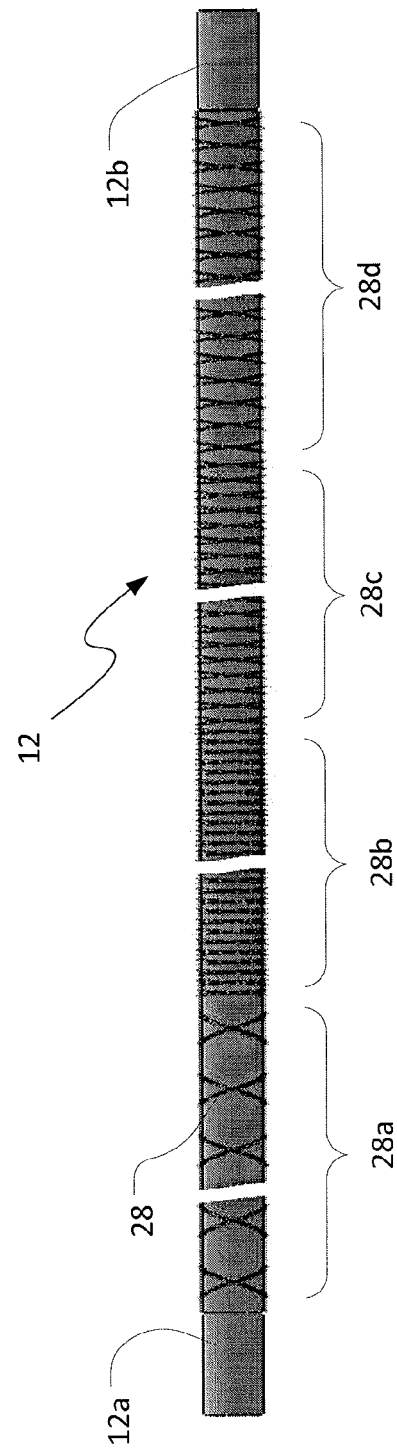
FIG. 1C is a side view of a schematic representation of a shaft of a microcatheter according to an embodiment of the invention displaying the winding of threads inside the side wall of the shaft.

Referring to FIG. 1C, the catheter shaft 12 may contain braids 28 along at least a portion of its length to provide reinforcement to the shaft 12 and reduce or prevent kinking. As noted herein, the braiding reinforcement preferably proceeds from relatively low pitch at the proximal end to relatively high pitch at the distal end. Since the hardness of the catheter wall 32 varies along the length of the shaft 12 from relatively high hardness (proximal end) to relatively low hardness (distal end) within sections 28a, 28b, 28c, and 28d, to compensate for the risk of kinking, the pitch of the braid 28 is therefore varied from the proximal end (relatively low pitch) to the distal end (relatively high pitch) as noted. The degree of reinforcement may also preferably be varied by selecting thread of varied thickness for the braid, such as 0.0005 inches to 0.005 inches, typically 0.001 inches of braid thickness. For example, a suitable braid thread may be a wire having a minimum tensile strength of 300 ksi (such as 304V0 SS). Other suitable materials for the thread include for example copper and copper alloys, tungsten, nitinol, gold, platinum, titanium, silver, or iridium, textiles, fibers, and high strength polymers. The pitch of the braid may be adjusted for the desired strength from 100-200 PPI (pics per inch), and any incremental value in between, for example, 100, 120, or 130 PPI for a relatively less flexible proximal end, 160, 170 or 180 PPI for a relatively flexible distal end, and 130, 140, or 150 PPI for intermediate sections (between the proximal and distal end). During manufacturing, the shaft 12 may include a further braided section having a very low pitch of 20-40 PPI (see section 28a in FIG. 1C), for ease of manufacturing. The low PPI in that area allows for an easier removal of the braid once the marker band is adhered to the shaft. To the left of the 28b is the soft tip that should not have the wire braid but should have the liner (FIG. 1A 26). The length of each of the sections 28a to 28d may vary from 1 inch to 50 inches. For example, section 28a may have a length of 1 to 5 inches, section 28b may have a length of 1.5 to 5 inches, section 28c may have a length of 5 to 10 inches, and section 28d may have a length of 30 to 50 inches.

The manufacturing process of the microcatheter may be summarized as follows. First, an inner tube such as PTFE tube is placed on a wire mandrel having an outer diameter that corresponds to the desired lumen diameter of the catheter to be made. The inner wire mandrel is used to prevent the tube from collapsing during the various manufacturing operations. The mandrel is attached to a machine with a predetermined screw thread. The mandrel is formed of silver plated copper. Then a reinforced spring coil is wrapped outside of the PTFE tube as is known in the art, with the distal open wound section formed by stretching. The spring is positioned concentrically around the PTFE tubular element. The spring extends from the proximal end of the catheter in a distal direction with different braid section and different winding pitches PPI. The coil spring enhances a variety of desirable properties, such as pushability, torqueability, and a resistance to kinking or compression by radially inwardly directed forces. The subassembly is then positioned within an exterior jacket such as different Shore D Hardness values of PEBAX™ nylon block copolymer tubing. The outer tubular jacket preferably extends throughout the length of the microcatheter to provide a relatively smooth exterior surface, but different stiffness characters from proximal to distal region. The outer jacket is thereafter exposed to a source of heat to shrink and laminate the jacket around the subassembly to provide a finished catheter body. Each region of flexibility, which is part and parcel of an outer layer, is formed in a continuous fashion to provide staged or graduated degrees or continuously variable degrees of flexibility according to a durometer reference. This therefore illustrates the construction of a single segment catheter which has increasing relative stiffness from the distal end of the catheter to the proximal end of the catheter.

The catheters also preferably incorporate a radiopaque marker at or near the distal tip and a proximal hub such as a luer fitting for connection to injection sources. A strain relief is also preferably included at the connection between the proximal hub and the proximal end of the catheter to prevent kinking. The entire length of the catheter is then dip coated with a hydrophilic coating solution to form predetermined thickness and smooth finished catheter.

The microcatheter of the invention is intended to facilitate injection of contrast media into all vessels, up to and including the cervical vessels, all vessels in the lower and upper extremities, visceral vessels and all coronary vessels. It is also intended for drug injection in intra-arterial therapy and embolic materials for haemostasis in procedures including, but not limited to, treatment of tumors or fibroids, such as Uterine Fibroid Embolization (UFE).

Typically, a medical practitioner would insert the catheter in the body of a patient, into the femoral artery, and navigate in the vasculature to the site of desired treatment with the aid of a positioning guide wire positioned within the lumen of the catheter. The travel of the catheter in the vasculature is monitored by fluoroscopy by following the displacement of the radiopaque marker positioned in the end piece of the catheter. Once in position in the blood vessel feeding the tumor or fibroid, a material may be introduced in the catheter and pushed there through to be deposited in the vessel at the site of the tumor or fibroid.

Figure 2:
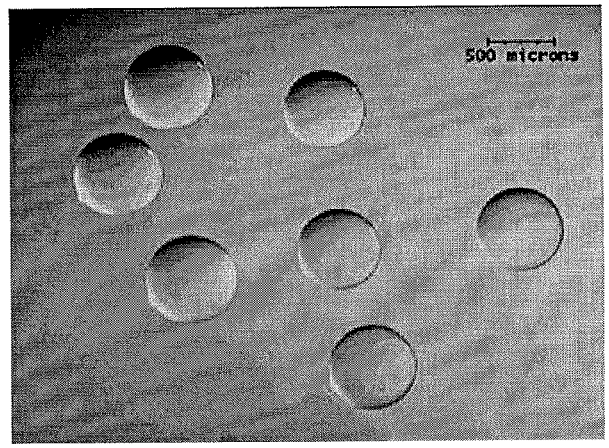
FIG. 2 is a photograph of microspheres of an embolic composition according to an embodiment of the invention without drug.
Figure 3:
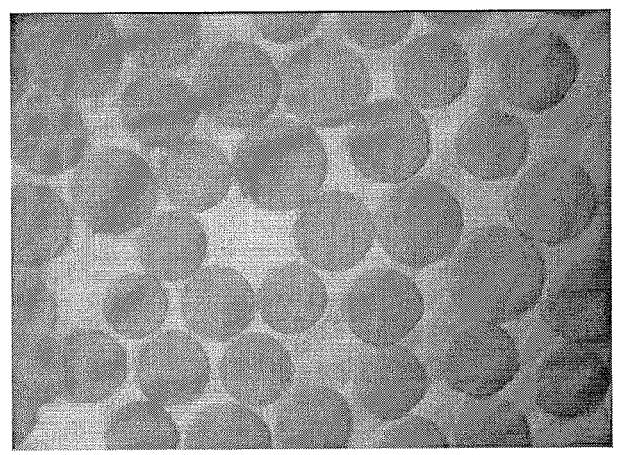
FIG. 3 is a photograph of microspheres of an embolic composition according to an embodiment of the invention with drug.
Figures 4, 5:
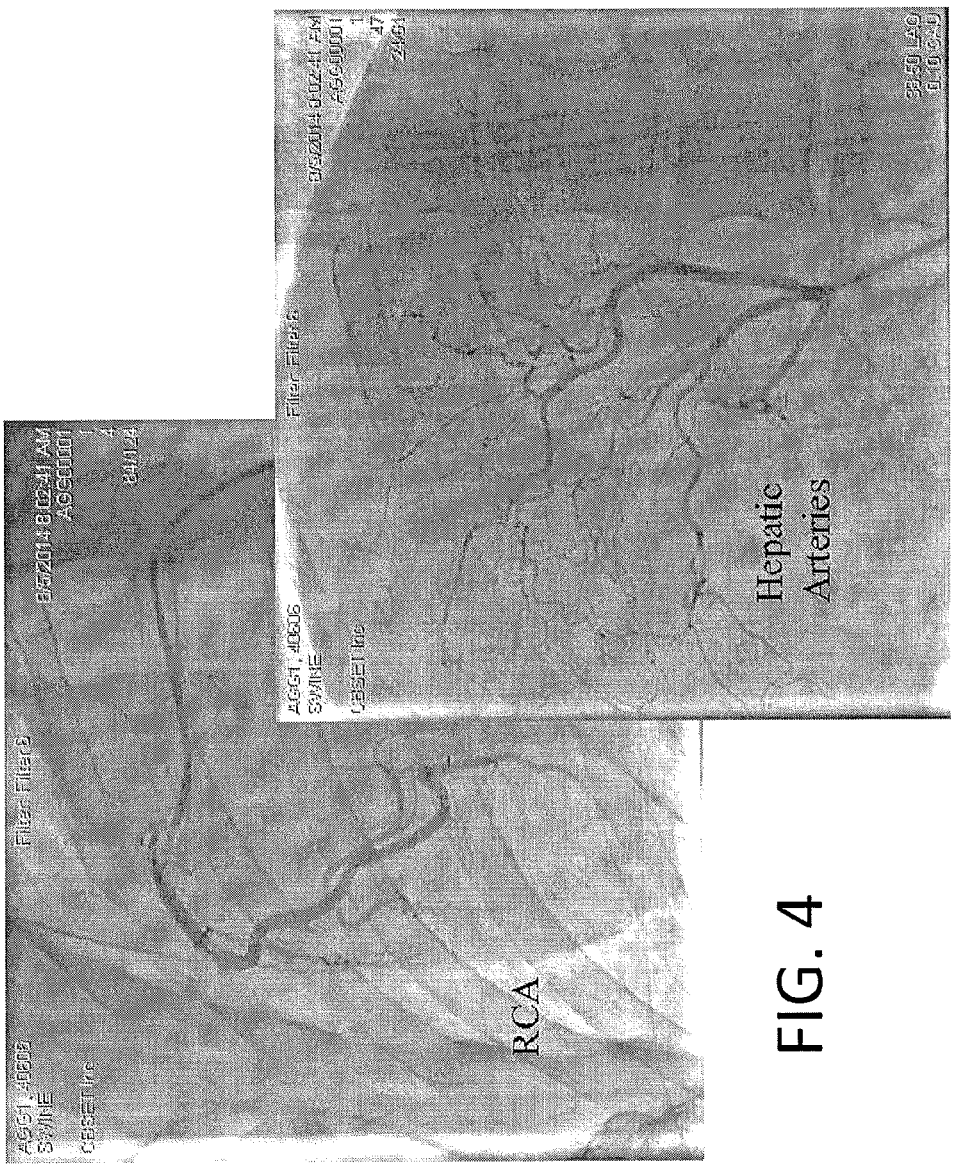
FIG. 4 is a radiography of the RCA (Right Coronary Artery) with contrast agent infused with a 5F guiding catheter (VISTA LONG BRITE TIP®; Cordis Corp; Bridgewater, N.J.).
FIG. 5 is a radiography of the hepatic arteries with contrast agent infused with 5F guiding catheter (VISTA LONG BRITE TIP®; Cordis Corp; Bridgewater, N.J.).
Figures 6, 7:
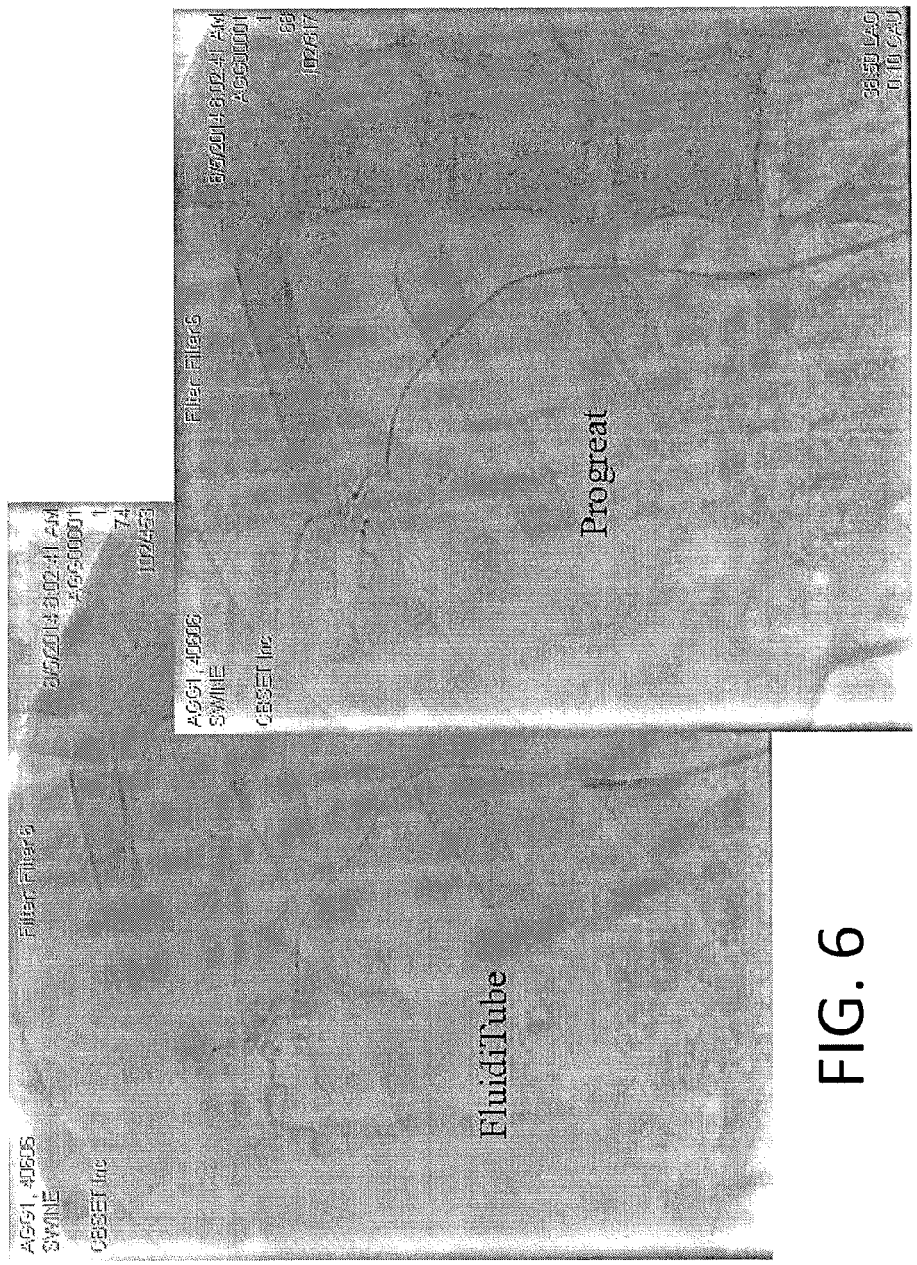
FIG. 6 is a radiography of the hepatic arteries with contrast agent infused with FluidiTube® microcatheter according to the invention.
FIG. 7 is a radiography of the hepatic arteries with contrast agent infused with Progeat microcatheter.
Figures 8, 9:
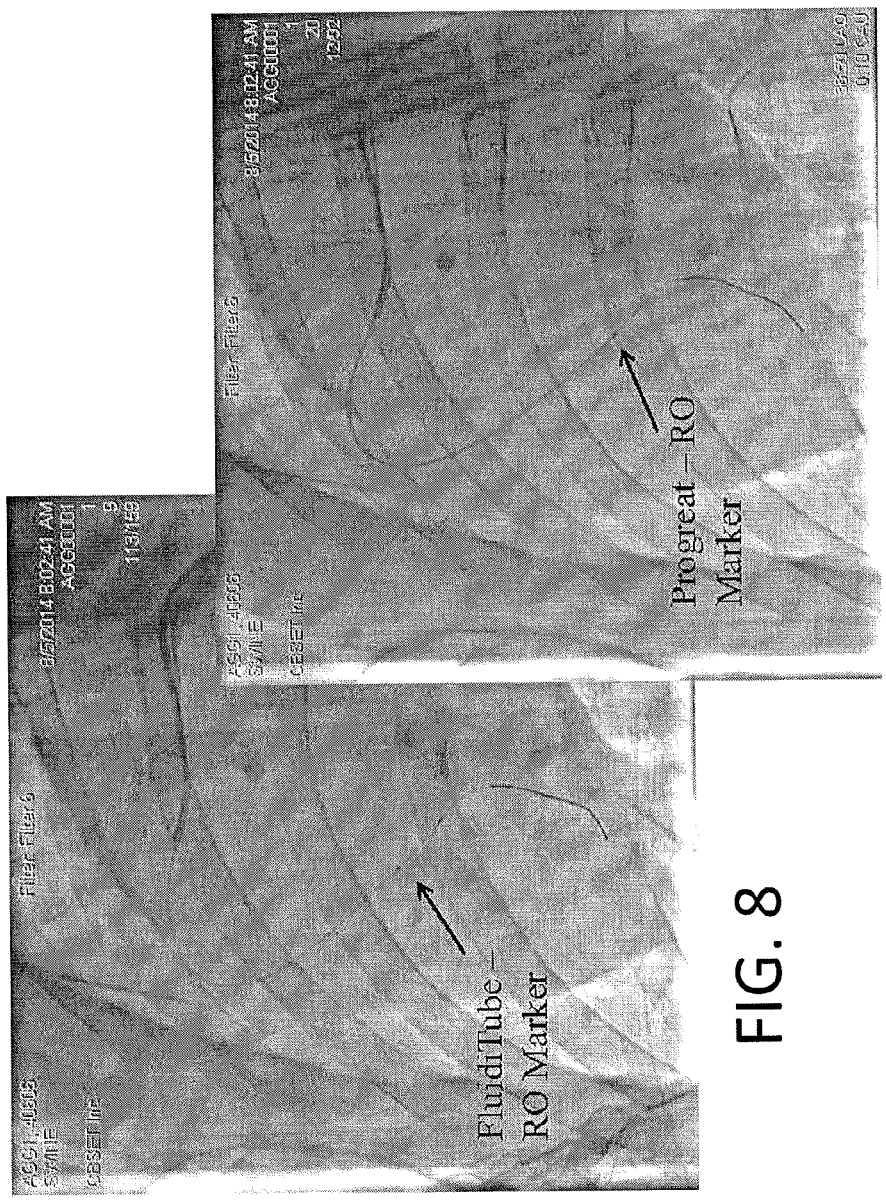
FIG. 8 is a radiography of the FluidiTube® microcatheter according to the invention in the RCA.
FIG. 9 is a radiography of the Progeat microcatheter in the RCA.
Figures 10, 11:
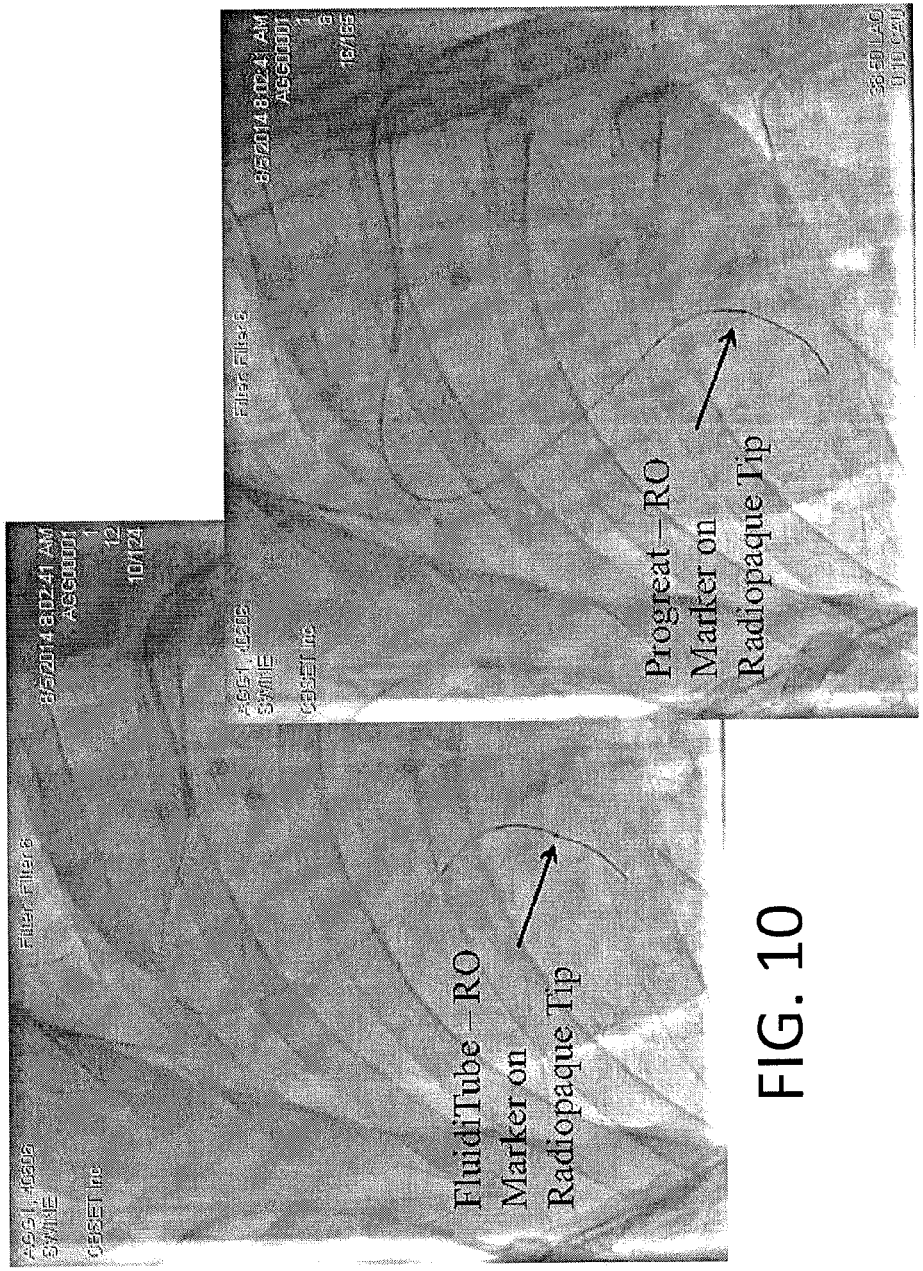
FIG. 10 is a radiography of the FluidiTube® microcatheter according to the invention in the RCA.
FIG. 11 is a radiography of the Progeat™ microcatheter in the RCA.
Figure 12:
FIG. 12 is a radiography of the FluidiTube® microcatheter according to the invention in the RCA artery with FIG. 4 as an insert.

Suitable compositions for injecting an embolization agent may include microsphere gel formulations of crosslinked hydrophilic polymers or copolymers. For example, a water soluble polymer or hydrophilic polymer such as polyvinyl alcohol, polyethylene glycol or macromolecular polysaccharide, such as amylose, chitosan and carboxymethyl cellulose, cellulose acetate and other macromolecules may be crosslinked to form a gel. The hydrophilic polymer may be functionalized with acrylic acid or derivatives. A microemulsion phase of the modified water soluble or hydrophilic polymer may be prepared by mixing with persulfate, tetramethyl ethylene diamine, or both, together with an initiator and a dispersing agent, to form an oil-water mixed reaction system. The use of 2-acrylamido-2-methylpropane sulfonic acid monomer forms a reversed-phase suspension to conduct the polymerization. Crosslinked, swellable microspheres are obtained as shown in FIGS. 2 and 3. An embolization agent may also be incorporated in the microspheres, such as a thrombolytic agent, and contrast agents. 2-acrylamido-2-methylpropane sulfonic acid monomer acts also as a dispersion stabilizer to more easily administer the microsphere compositions. Dyes or pigments may also be incorporated into the microspheres to identify a microsphere composition having a specific embolization agent, for example, such as reactive blue dye, reactive yellow dye, according to the requirements of the surgical condition being treated, such as shown in FIG. 3.

The prepared microspheres with the embolization agent may be prepared with relatively uniform particle geometry, good dispersibility, near perfect spherical appearance, and can be separated according to different needs in a range of different particle sizes, such as 100-300 μm, 300-500 μm, 500-700 μm, 700-900 μm and 900-1200 μm. Such microsphere compositions may be used in treatments of fibroids, such as uterine fibroids embolization, primary metastatic liver, brain, bone, kidney, uterus and other cancer treatments, such as hepatoma cells embolism. The microspheres have good stretching deformation resistance or better elastic characters and can be restored even after 50% or more compression to the original state. Therefore, during the procedure, the microspheres, optionally loaded with the embolization agent, may be easily passed through the fine lumen of the microcatheter of the invention without plugging, and will be deposited at the treatment site. The embolization microsphere compositions also have a strong fixity at target site, i.e. remain at the injection site permanently, sufficient to trigger necrosis of the tumor/fibroid or tumor/fibroid shrinkage.

EXAMPLES

Example 1

Flow Rate Study

A microcatheter having a tapered shaft composed of two segments, each having different outer diameters (1.7 F and 2.1 F; 2.7 F and 2.9 F; or 2.8 F and 3.0 F) is provided as presented in Table 1 below. The catheter has a semi rigid proximal shaft which becomes progressively more flexible toward the distal end. The shaft is reinforced with braids. The distal portion of the shaft (70 cm) is coated with a hydrophilic material prepared with Lubricent primer solution combined with Lubricent hydrophilic coating solution (LB010460 by Harlan Medical Systems, Eden Prairie, Minn.). The lumen is lined with a lubricious material to facilitate movement of guidewires and other devices through the lumen of the catheter.

TABLE 1

| Device configuration: | | | | | |
|---|---|---|---|---|---|
| Profile size | Transitions to | OD distal end | OD proximal end | Lumen ID | Usable Length |
| 1.7F | 2.1F | 0.0229" Max | 0.02811" Max | 0.017" | 150 cm |
| 2.7F | 2.9F | 0.0360" Max | 0.03821" Max | 0.025" | 110 cm |
| | | | | | 130 cm |
| 2.8F | 3.0F | 0.03678" Max | 0.03957" Max | 0.027" | 130 cm |

Flow rates for specific viscosity of glycerin-water mixtures have been measured according to diameter, length of the catheter and applied pressure. The results are presented in Table 2 below.

TABLE 2

| Flow Rates | | | | | | |
|---|---|---|---|---|---|---|
| | | Set Condition of Glycerin-Water Mixture | | Set Condition of Test Equipment | | |
| Microcatheter Size; Distal/Proximal (mm) | Usable Length (cm) | Viscosity (cP) | Volume (mL) | Flow-Rate (mL/sec) | Pressure kPa (psi) | Average Flow-Rate (mL/sec) |
| 2.7F/2.9F (0.90/0.97) | 110 | 4.4 | 20 | 6.0 | 4137 (600) | 4.2 |
| | | | | | 5171 (750) | 4.8 |
| | | 9.1 | 10 | 3.0 | 4137 (600) | 2.3 |
| | | | | | 5171 (750) | 2.6 |
| | 130 | 4.4 | 20 | 6.0 | 4137 (600) | 3.7 |
| | | | | | 5171 (750) | 4.3 |
| | | 9.1 | 10 | 3.0 | 4137 (600) | 2.0 |
| | | | | | 5171 (750) | 2.4 |

These are the results of power injection test performed under guidance of ISO 10555-1:2013. A low flow rate should be applied when injecting high viscous solution. The average flow rate shows minor difference, especially if the catheter is shorter.

Example 2

Catheter

A microcatheter having a tapered shaft composed of two segments, each having different outer diameters (2.7 F and 2.9 F) is shown in FIGS. 1A-1C. The catheter has a semi rigid proximal shaft which becomes progressively more flexible toward the distal end. The shaft is reinforced with braids. The utmost distal portion of the shaft (0.15 cm; 0.06 inch) has no braids and is covered with a copper tip with a rounded edge. A fluoroscopic marker band is disposed near the distal tip and is made of platinum enriched with 10% iridium and secured to the tubing with a cyanoacrylate glue. The length and pitch (PPI) of the braided sections are set forth in Table 3 below. The braid wire material is 304V0 SS, having 300 ksi tensile strength minimum. The distal portion of the shaft (70 cm; 27.6 inch) is coated with a hydrophilic material prepared with Lubricent primer solution combined with Lubricent hydrophilic coating solution. The lumen has in internal diameter of 0.025 inch throughout the length of the shaft. The lumen has a PTFE liner 0.0005 inch thick to facilitate movement of guidewires and other devices.

TABLE 3

Catheter specifications

| Section length* (in) | Outer diameter (in) | Wall thickness (in) | Braid pitch (PPI) | Material | FIGS Sections Identifiers |
|---|---|---|---|---|---|
| 0.06 | 0.0425 | 0.0027 | — | PeBax30D - 20% BaSO$_4$ | 12a, 32a |
| 2.7 | 0.0425 | 0.0027 | 160 | PeBax30D - 20% BaSO$_4$ | 12a, 28b, 32a |
| 3.9 | 0.0425 | 0.0027 | 150 | PeBax30D - 20% BaSO$_4$ | 12a, 28c, 32a |
| 1.6 | 0.0425 | 0.0027 | 150 | PeBax45D - 20% BaSO$_4$ | 12a, 28c, 32b |
| 1.6 | 0.0425 | 0.0027 | 150 | PeBax55D - 20% BaSO$_4$ | 12a, 28c, 32c |
| 1.6 | 0.0445 | 0.0037 | 150 | PeBax72D - 20% BaSO$_4$ | 12b, 28c, 32d |
| 39.8 | 0.0445 | 0.0037 | 120 | Aeson Nylon 12 (75D)-20% BaSO$_4$ | 12b, 28d, 32e |

*From distal to proximal end.

Example 3

Microsphere Preparations with PVA-Cellulose Acetate 100 g of polyvinyl alcohol (PVA) ($2 \times 10^4$-$5 \times 10^4$ average molecular weight) was added to 500 g of water. The mixture was stirred at a speed of 190 RPM and heated to 90° C. for 2 hrs till PVA fully dissolved. After cooled to room temperature, 1.2 g of sodium acrylate was added to the solution and stirred at a speed of 190 RPM for 6 hrs. The crude product was vacuum dried to give a functionalized PVA gel, which may be stored below room temperature.

1.63 g of 2-acrylamido-2-methylpropane sulfonic acid and 1.034 g potassium persulfate were fully dissolved in 17.3 g of water. 40 g of functionalized PVA gel (prepared in step 0002) was added to the solution and stirred to generate a polymerizable monomer solution. To the 240 mL butyl acetate was added 4.55 g of cellulose acetate. After stirred at 240 RPM for 10 min., the solution was heated to 68° C. under N$_2$ atmosphere. When the temperature of the solution reached 65° C., the stirring speed was adjusted to 190 RPM and the PVA monomer solution was added to the reaction gradually. After stirring for 10 min., 0.78 mL of tetracarboxylic ethylene diamine was added to the reaction. The reaction was stirred continuously for 6 hrs. The reaction mixture was cooled, filtered, and the filter cake was washed with butyl acetate and then ethyl acetate several times, and then vacuum-dried to give the desired microspheres. The microspheres present nearly perfect spherical shape, smooth surface. The diameter range is 1~1500 µM, and its compression deformation ratio is 50% or more. The microspheres can be injected with micro catheters with the following specifications.

TABLE 4

Compatibility of microspheres in function of catheters' internal diameters.

| | Microspheres Sizes | | | | |
|---|---|---|---|---|---|
| Micro Catheter Size | <<300 (µm) | <<500 (µm) | <<700 (µm) | <<900 (µm) | <<1200 (µm) |
| ≥4.0Fr | ✓ | ✓ | ✓ | ✓ | ✓ |
| ≥3.0Fr | ✓ | ✓ | ✓ | ✓ | |
| ≥2.7Fr | ✓ | ✓ | ✓ | | |
| ≥2.5Fr | ✓ | ✓ | | | |
| ≥1.7Fr | ✓ | | | | |

The data of in vitro and in vivo in animal test and clinical trial indicated that the microspheres possess good biocompatibility and stability in normal saline, and can be stored at room temperature for more than 2 years.

Example 4

PVA-Cellulose Acetate Dyed Microspheres 1 kg of the microspheres prepared according to Example 3 were washed by stirring with water for 15 min. then filtered out. The washing process was then repeated twice. Then 2 kg of water was added to the washed microspheres. The mixture was stirred to form a microsphere suspension. 0.2 g of Reactive Blue dye was added to the microsphere suspension and stirred at room temperature for 20 min. Upon the completion of colorization, the tinted microspheres were washed three times with water and then filtered. The microspheres were re-dispersed in water and boiled for 15 min. then filtered to give blue microspheres as a colored embolic agent. The colored microspheres were stored in saline. After staining, the microspheres were easy to be identified both in vivo and in vitro.

Example 5

Amylose-Cellulose Acetate Microspheres 100 g of amylose ($4\times10^4$~$5\times10^4$ average molecular weight) was added to 500 g of water. The mixture was stirred at 190 RPM and heated to 90° C. for 3 hrs. until fully dissolved. After cooled to room temperature, 1.2 g sodium acrylate was added to the solution. The mixture was stirred at a speed of 190 RPM for 6 hrs. The crude product was dried under vacuum to give a functionalized amylose gel, which could be stored at room temperature or below.

1.83 g of 2-acrylamido-2-methyl propane sulfonic acid and 1.054 g of potassium persulfate were fully dissolved in 20.3 g of water. 40 g of functionalized amylose gel was added to the solution and stirred to generate a monomer solution. To the 300 mL butyl acetate was added 4.65 g of cellulose acetate. Under $N_2$ atmosphere, the mixture was stirred at speed of 360 RPM for 10 min then heated to 68° C. When the temperature of reaction reached 65° C., the stirring speed was adjusted to 290 RPM and the amylose monomer solution was added gradually. After the addition, the reaction was stirred for 10 min then 0.78 mL of tetramethyl ethylene diamine was added. After 8 hrs, the reaction mixture was cooled to room temperature and crude product was filtered out. The filtered crude product was washed with butyl acetate then ethyl acetate several times and then vacuum-dried to give desired microspheres. The microspheres present nearly perfect spherical shape, smooth surface, the diameter range is 1~1500 μM and its compression deformation ratio is 50% or more (shown in FIG. 2).

Example 6

Microspheres Preparation with Yellow Dye 1 kg the microspheres prepared according to Example 5 were washed by stirred with water for 15 min. then filtered out. The washing process was then repeated twice. 2 kg of water was added to the washed microspheres. The mixture was stirred to form a microsphere suspension. 0.2 g of Reactive Yellow dye was added to the microsphere suspension and stirred at room temperature for 20 min. Upon the completion of colorization, the tinted microspheres were washed three times with water and then filtered. The microspheres were re-dispersed in water and boiled for 15 min. then filtered to give blue microspheres as a colored embolic agent (shown in FIG. 3). The colored microspheres were stored in saline.

Example 7

Microsphere Preparations with Chitosan-Cellulose Acetate 150 g of chitosan ($2\times10^4$~$4\times10^4$ average molecular weight) was added to 500 g of water and heated to 95° C. with stirring at a speed of 190 RPM about 3 hrs. After cooled to room temperature, 1.5 g of ethyl acrylate was added to the solution. The mixture was stirred at a speed to 190 RPM for 5.5 hrs. The crude product was dried under vacuum to give a functionalized chitosan gel, which may be stored at room temperature or below.

1.82 g of 2-acrylamido-2-methylpropane sulfonic acid and 1.055 g of potassium persulfate were fully dissolved in 20.1 g of water. 40 g of the above functionalized chitosan gel was added to the solution. The mixture was stirred to generate an even polymerizable monomer solution. To the 300 mL of butyl acetate was added 4.65 g of cellulose acetate. Under N2 atmosphere, the mixture was stirred at a speed of 360 RPM for 10 min. then heated to 68° C. As the temperature of reaction system reached 65° C., the stirring speed was adjusted to 290 RPM and the functionalized chitosan gel monomer solution was added gradually. After the addition, the reaction mixture was stirred for 10 min. then 0.78 mL of tetramethyl ethylene diamine was added. The reaction was stirred for 8 hrs. The mixture was cooled to room temperature and microspheres were filtered out. The filtered crude product was washed several times with butyl acetate, then ethyl acetate, and then vacuum-dried to give microspheres. The microspheres present nearly perfect spherical shape, smooth surface. The diameter range is 1~1500 μM and its compression deformation ratio is 50% or more.

Example 8

Microsphere Preparation with Blue Dye 1 kg the microspheres prepared according to Example 7 were washed by stirred with water for 15 min. then filtered out. The washing process was then repeated twice. At least 2 kg of water was added to the washed microspheres. The mixture was stirred to form a microsphere suspension. 0.2 g of Reactive Blue dye was added to the micro sphere suspension, stirred at room temperature for 20 min., washed three times with water and then filtered. The filter cake was re-dispersed in water and boiled for 15 min., then filtered to give blue microspheres as a colored embolic agent. The colored microspheres was stored in saline.

Example 9

Microsphere Preparations with Hydroxymethyl Cellulose-Cellulose Acetate 100 g of hydroxymethyl cellulose (HMC) ($3\times10^4$~$4\times10^4$ average molecular weight) was added to 500 g of water. The mixture was stirred at speed of 190 RPM and heated to 90° C. for 2.5 hrs. until the hydroxymethyl cellulose was fully dissolved. After cooled to room temperature, 1.0 g of methyl acrylate was added the solution. The mixture was stirred at a speed to 190 RPM to allow the completion of the reaction. The crude product was dried under vacuum to give a gel-like functionalized HMC. The compositions may be stored below room temperature.

1.80 g of 2-acrylamido-2-methylpropane sulfonic acid and 1.05 g of potassium persulfate were fully dissolved in 20 g of water. 40 g of functionalized HMC was then added to the solution and stirred to give a polymerizable monomer even solution. 4.65 g cellulose acetate was added to 300 mL of butyl acetate. The mixture was stirred at speed of 300 RPM for 10 min. then heated to 68° C. under $N_2$ atmosphere. As the temperature of reaction system reached 65° C., the stirring speed was adjusted to 250 RPM and the monomer solution was added gradually. After stirred for 10 min., 0.75 mL of tetramethyl ethylene amine was then added to the reaction and stirred continuously for 8 hrs. The reaction mixture was cooled, filtered, and washed several times with butyl acetate then ethyl acetate. The product was then vacuum-dried to give the microspheres. The microspheres present nearly perfect spherical shape, smooth surface. The diameter range is 1~1500 µM, and its compression deformation ratio is 50% or more.

Example 10

Microsphere Preparations with Blue Dye 1 kg the microspheres prepared according to Example 9 were washed by stirred with water for 15 min. then filtered out. The washing process was then repeated twice. 2 kg of water was added to the washed microspheres. The mixture was stirred to form a microsphere suspension. 0.2 g of Reactive Blue dye was added to the microsphere suspension and stirred at room temperature for 20 min. The mixture was washed three times with water and then filtered. The filtered crude product was re-dispersed in water and boiled for 15 min. After the filtration, blue microspheres was obtained as a colored embolic agent. The colored microspheres was stored in saline.

Example 11

Microsphere Preparations with Polyethylene Glycol-Cellulose Acetate 200 g of polyethylene glycol (PEG) ($3 \times 10^4$~$4 \times 10^4$ average molecular weight) were added to 500 g of water. The mixture was then stirred at speed of 100 RPM and heated to 80° C. for 2.5 hrs till fully dissolved. The polyethylene glycol solution was cooled to room temperature. 2.0 g of butyl acrylate was added and stirred at a speed to 120 RPM for 4 hrs. Upon the full completion of the reaction, the crude product was vacuum dried to obtain a gel-like functionalized PEG, which may be stored at room temperature or below.

1.73 g of 2-acrylamido-2-methylpropane sulfonic acid and 1.044 g of potassium persulfate were fully dissolved in 18.8 g water. Then, 45 g of the above functional PEG were added to the solution and stirred evenly to generate, a polymerizable monomer solution. 4. 60 g of cellulose acetate were added to 270 mL of butyl acetate and stirred at a stirring speed of 300 RPM for 10 min. Under $N_2$ atmosphere, the mixture was stirred and heated to 68° C. When the temperature reached 65° C., the stirring speed was adjusted to 240 RPM. The functionalized PEG monomer solution was then added to reaction mixture. After stirred for 10 min, 0.78 mL of tetramethyl ethylene diamine, and the reaction was stirred for 7 hrs. After cooled to room temperature, the crude product was washed with butyl acetate and ethyl acetate, several times, and then vacuum-dried to give microsphere. The microspheres present nearly perfect spherical shape and smooth surface. The diameter range is 1~1500 µM and its compression deformation ratio is 50% or more.

Example 12

Microsphere Preparations with Blue Dye 1 kg of the microspheres prepared according to Example 11 were washed by stirred with water for 15 min. then filtered out. The washing process was then repeated twice. 2 kg of water was added to the washed microspheres. The mixture was stirred to form a microsphere suspension. 0.2 g of Reactive Blue dye was added to the microsphere suspension and stirred at room temperature for 20 min. then washed three times with water and filtered. The filter cake was re-dispersed in water and boiled for 15 min. After filtration, the blue colored microspheres were obtained as a colored embolic agent. The colored microspheres were stored in saline.

Example 13

Swine Study

Procedure and Materials

One male Yorkshire swine underwent an interventional procedure in which two (2) Interventionalists/Operators evaluated the acute performance of microcatheter according to Example 2 (FluidiTube® 2.7 Fr Microcatheters) compared to a marketed control device (Progreat 2.7 Fr Microcatheter System [Terumo, Somerset, N.J.]) in the coronary, hepatic and iliac arteries. Each Interventionalist evaluated the same 5 tests and 2-3 control articles in each artery. For each catheter, fluid compatibility (heparin and contrast) and embolic microspheres 500-700 µm (prepared according to Example 4) compatibility were tested one time in the hepatic artery. Each device was evaluated for acute performance characteristics, including retrieval of the catheter from the packaging, tip shapability, trackability, guidewire compatibility, radiopacity, fluid compatibility, embolic compatibility, and device integrity. The evaluation was graded against the Interventionalists' experience with performing peripheral and coronary artery interventions in this model and in performing embolic procedures using microcatheters. User needs criteria were rated as Acceptable or Unacceptable.

Electrocardiograms, heart rate, respiratory rate, $SpO_2$, and temperature were monitored and documented at regular intervals during the anesthetic procedure. When possible, blood pressure (direct) was monitored and documented at regular intervals during the procedure.

Fluoroscopy was used to qualitatively evaluate parameters such as vascular anatomy, implant site suitability, and/or acute deployment characteristics. The angiograms were recorded in digital format and transferred to digital storage media.

User handling criteria, including retrieval of the catheter from the packaging, tip shapability, trackability, guidewire compatibility, radiopacity, fluid compatibility, embolic compatibility, and device integrity were rated as either Acceptable or Unacceptable. Activated clotting times were monitored during the interventional procedure. Fluoroscopy was used qualitatively to evaluate parameters such as vascular anatomy, treatment site suitability, acute deployment characteristics, and vascular injury/dissection. Removed catheters were examined for the presence of thrombus.

Telazol® (4 mg/kg, IM) was administered as a pre-anesthetic. Isoflurane anesthesia (delivered in 100% oxygen) was administered. The animal was placed in dorsal recumbency. After induction of anesthesia, vascular access was made in the right and left femoral arteries via percutaneous approach. An introducer sheath was advanced and heparin (150 U/kg, IV) was administered to prolong ACT to a target of minimally 275 (−15) seconds. A blood sample (<0.5 mL) was collected within 7 minutes of heparin administration to confirm the ACT value had reached the ACT target value. Additional tests were run at intervals of 45±5 minutes. Heparin (150 U/kg, IV) was administered when needed to maintain the target ACT.

Under fluoroscopic guidance, a 5F guiding catheter (VISTA LONG BRITE TIP®; Cordis Corp; Bridgewater, N.J.) was tracked over a 0.035" guidewire into the right coronary artery (RCA). Angiography was performed after administration of nitroglycerin (200 µg). Using the 0.014" BMW coronary guidewire, the Interventionalist evaluated 5 test and 2 control articles in the RCA and acute performance characteristics were evaluated. Angiography of the hepatic arteries was performed after administration of nitroglycerin (200 µg). Using the 0.021" Glidewire peripheral guidewire, the Interventionalist then evaluated the same 5 test and 2 control articles in the hepatic arteries. Angiography of the contralateral iliac artery was performed after administration of nitroglycerin (400 µg). Using the V-18™ ControlWire™ 0.018" peripheral guidewire the Interventionalist then evaluated the same 5 test and 2 control articles in the iliac artery. For each catheter, fluid compatibility (heparin and contrast) and embolic microsphere compatibility were tested one time in the hepatic artery.

The second Interventionalist followed the same procedure with 5 new test articles and 3 new control articles with the exception of nitroglycerin administration which was only given as needed to treat vasospasm.

Results:

FluidiTube 2.7 Fr Microcatheters: Both Operators rated the ability to flush the packaging hoop and remove the FluidiTube Microcatheter from the hoop without damage as acceptable for all microcatheters. Prior to introducing the FluidiTube Microcatheter into the animal for the first time, both Operators shaped the tip of the microcatheter with a mandrel and rated this as acceptable for all microcatheters. Once inserted into the animal, the operators rated the compatibility of the FluidiTube Microcatheter with the guidewire (0.014 in the RCA, 0.021 in the hepatic artery, and 0.018 in the iliac artery) as acceptable for all microcatheters. The ability to track the FluidiTube Microcatheter through all three vessels and visualize them fluoroscopically was rated acceptable for all microcatheters by both Operators. In the hepatic artery, 1 mL of heparin, 2 mL of non-dilute contrast media, and 1 mL of 500-700 µm embolic microspheres (prepared according to Example 4) were injected through each FluidiTube Microcatheter; both Operators rated compatibility as acceptable for all microcatheters. Both Operators rated the integrity of the FluidiTube Microcatheter as acceptable, with no kinking or damage to the tip of any microcatheter. After each evaluation, the catheter was removed from the animal and examined for the presence of thrombus; none was observed.

Progreat 2.7 Fr Micro Catheters: Both Operators rated the ability to flush the packaging hoop and remove the Progreat Microcatheter from the hoop without damage as acceptable for all microcatheters. Prior to introducing the Progreat Microcatheter into the animal for the first time, both Operators shaped the tip of the microcatheter with a mandrel and rated this as acceptable for all microcatheters. Once inserted into the animal, the operators rated the compatibility of the Progreat Microcatheter with the guidewire (0.014 in the RCA, 0.021 in the hepatic artery, and 0.018 in the iliac artery) as acceptable for all microcatheters. The ability to track the Progreat Micro Catheter through all three vessels and visualize them fluoroscopically was rated acceptable for all microcatheters by both Operators. In the hepatic artery, 1 mL of heparin, 2 mL of non-dilute contrast media, and 1 mL of 500-700 µm embolic spheres were injected through each Progreat Microcatheter; both Operators rated compatibility as acceptable for all microcatheters. Both Operators rated the integrity of the Progreat Microcatheter as acceptable, with no kinking or damage to the tip of any microcatheter. After each evaluation, the catheter was removed from the animal and examined for the presence of thrombus; none was observed.

The advantages of the FluidiTube microcatheter over the Progreat microcatheter observed from the FIGS. 4-12 from this comparison animal study were the followings: 1) FluidiTube microcatheter tip was softer and had a high degree of flexibility that facilitated negotiation of small, tortuous vessels such as those encountered in intercranial catheterizations; 2) The mark band of FluidiTube microcatheter was narrower, but could easily be detected under fluoroscopy FluidiTube microcatheter was easy to bend to navigate in difficult and narrow blood vessels such as having more than 90 degree turn; 3) The injection of 500-700 µm embolic microspheres was much easier and presents less resistance; 4) The braided structure of FluidiTube microcatheter made it more resistant to kinking.

Example 14

Microspheres Loaded with Doxorubicin

Polyvinyl alcohol (PVA) hydrogel based microspheres (Callispheres™) modified with charged sulfonate groups may be prepared to have the capacity to carry commonly used chemotherapeutic drugs, such as doxorubicin HCl by ionic bonds and H-bonds as shown below.

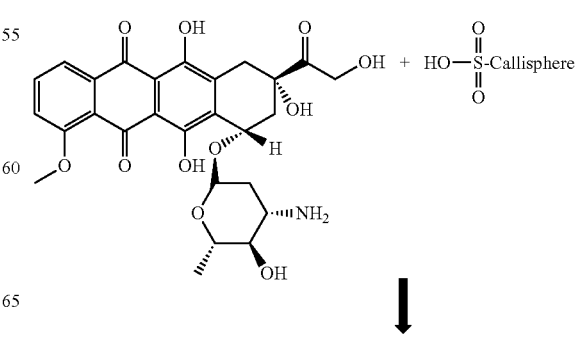

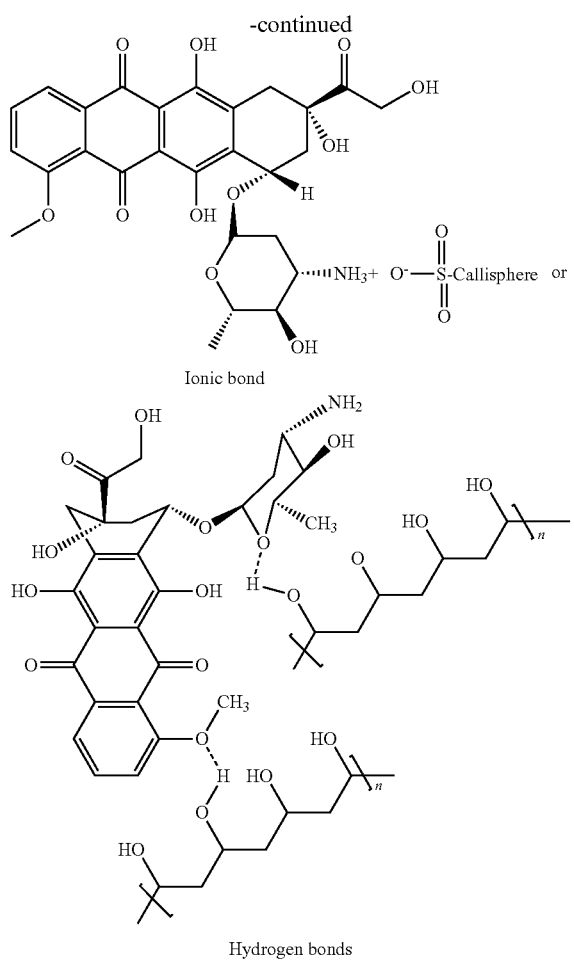

Microspheres prepared according to Example 3 were prepared according to a modified procedure as follows. Instead of 1.2 g of sodium acrylate, 2.4 g of N-acryloyl-aminoacetaldehyde dimethylacetal was added to the solution and stirred at a speed of 190 rpm for 6 hrs. Instead of 1.63 g, 21.20 g of 2-acrylamido-2-methylpropane sulfonic acid and 7.034 g potassium persulfate were fully dissolved in 150.3 g of water. After stirring for 10 min., instead of 0.78 mL of tetracarboxylic ethylene diamine, 8.85 mL N,N,N', N'-Tetramethylethylenediamine was added to the reaction. The remaining process steps were the same as in Examples 3 and 4. Thus the negative charged sulfonate groups in microspheres will have the capacity to carry commonly used chemotherapeutic drugs, such as positive charged Doxorubicin HCl, Epirubicin, Pirarubicin, and Irinotecan by ionic bonds.

Figure 13:
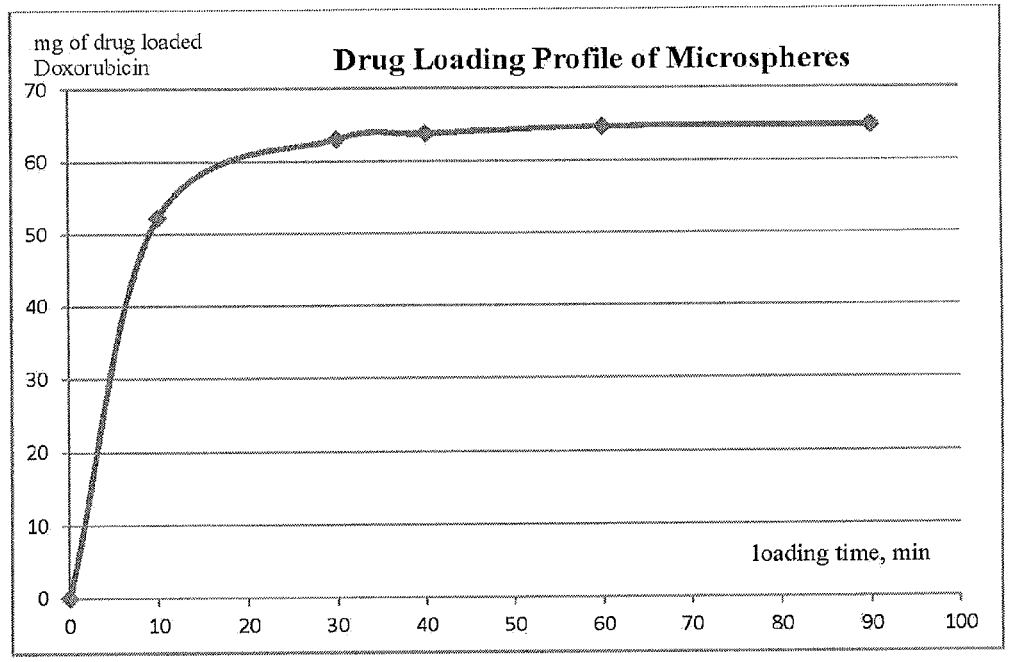
FIG. 13 is a plot of the loading profile of Doxorubicine with Sulfonated PVA microspheres prepared according to example 14 (mg drug v. min.). And, FIG. 14 is a plot of the accumulated release profile of doxorubicine according to example 14 (% drug v. days).

FIG. 13 shows the loading profile of the microspheres with doxorubicin. It took 30 mins. to load 60% of doxorubicine.

Figure 14:
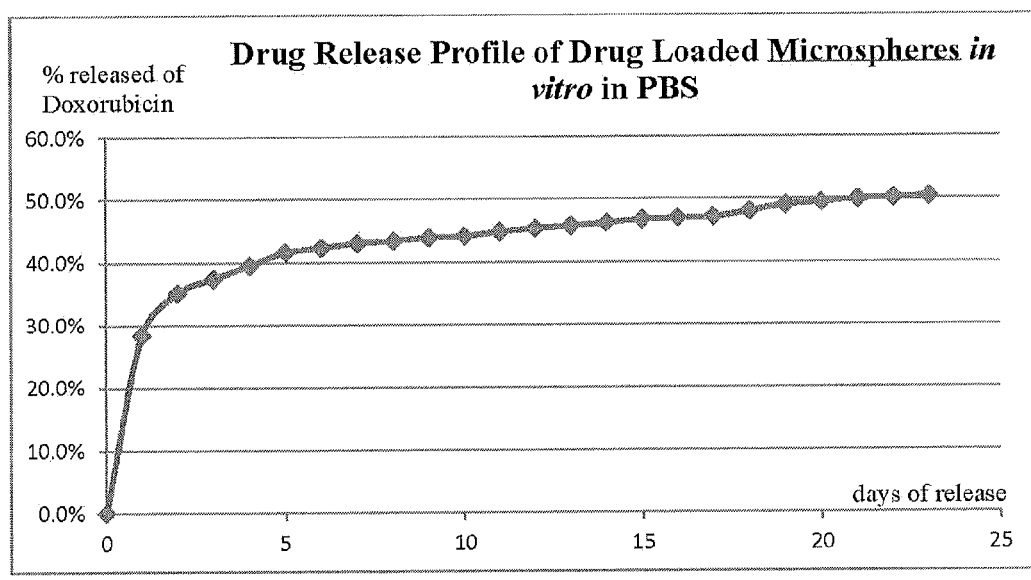

FIG. 14 shows the release profile of the drug loaded to microspheres in PBS. The release profile data was collected by the following means: 500 mL pH 7.3 PBS solution was kept at 37° C. in a glass flask, 1.0 g drug-loaded microspheres was wrapped in a stainless steel screen mesh (500 mesh, or 25 μm) and suspended in the solution. The solution was stirred at 60 rpm and concentration of the drug was followed aver time. A HPLC method was used to measure the drug release from microspheres. A sample of 0.5 mL PBS solution was collected from every timing point and filtered through a 45 μm filter the solution, then injected into HPLC and the drug concentration in the solution was calculated. The PBS solution was emptied out and replaced by fresh 500 mL of PBS solution every two days in the glass flask until the completion of the test.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A method of conducting a medical procedure in the blood vessel of a patient comprising:
    inserting a catheter into the femoral artery of a patient wherein said catheter comprises
        a hub having a proximal and distal end;
        a luer adapter disposed at the proximal end for connecting with medical equipment;
        a shaft extending from the hub distal end, the shaft having a proximal end, a distal end, a length of at least 35 inches, and a lumen, the shaft comprising
            at least a first segment and a second segment each providing a portion of the length of the shaft, the first and second segments each having an outer diameter, the first segment outer diameter larger than the second segment outer diameter and the first segment arranged proximal to the second segment;
            at least three braid sections each providing a portion of the length of the shaft, the at least three braid sections comprising a first braid section at the proximal end with a winding pitch of 100-130 PPI, a second braid section between the proximal end and distal end with a winding pitch of 130-150 PPI, and a third braid section at the distal end with a winding pitch of 160-180 PPI;
            an outer jacket overlying the at least three braid sections, the outer jacket having a plurality of regions each providing a portion of the length of the shaft, the plurality of regions having different Shore D hardness values and arranged such that a Shore D hardness value at the proximal end is greater than at the distal end, and the plurality of regions having different wall thickness and arranged such that a wall thickness at the proximal end is greater than at the distal end;
    navigating the distal end of the catheter to a site of treatment in the blood vessel of a patient;
    introducing a composition comprising hydrogel microspheres into the lumen of the shaft of the catheter, wherein at least a portion of the hydrogel microspheres have a diameter greater than a diameter of the lumen of the catheter, and wherein the hydrogel microspheres have a diameter in a range of 500-700 μm and are deformable and have a compression deformation ratio of at least 50%;
    injecting the composition comprising hydrogel microspheres from the lumen into the blood vessel.

2. The method of claim 1 wherein the microspheres comprise a crosslinked copolymer of cellulose acetate and a hydrophilic polymer.

3. The method of claim 2 wherein the hydrophilic polymer is selected from a poly alkylene glycol, polysaccharide, glucosaminoglycan, and modified cellulose.

4. The method of claim 2 wherein the hydrophilic polymer is selected from hydroxymethyl cellulose, chitosan, amylose, cellulose acetate, and polyvinyl alcohol.

5. The method of claim 2 wherein the microsphere further comprises a dye.

6. The method of claim 2 wherein said composition comprises a therapeutic agent.

7. The method of claim 2 wherein the site of treatment is an artery in the liver, heart, kidney, or uterus.

8. The method of claim 2 wherein the site of treatment is a blood vessel in a tumor or fibroid.

9. The method of claim 2 further comprising injecting an anticoagulant.

10. The method of claim 2 wherein the microspheres comprise a fluoroscopic agent.

11. The method of claim 10 further comprising imaging blood vessels at the site of treatment.

\* \* \* \* \*